US006975907B2

(12) United States Patent
Zanakis et al.

(10) Patent No.: US 6,975,907 B2
(45) Date of Patent: Dec. 13, 2005

(54) APPARATUS AND METHOD FOR REPAIR OF SPINAL CORD INJURY

(75) Inventors: Michael J. Zanakis, Stuart, FL (US); Philip A. Femano, Nutley, NJ (US)

(73) Assignee: DynaMed Systems, LLC, New York, NY (US)

(*) Notice: Subject to any disclaimer, the term of this patent is extended or adjusted under 35 U.S.C. 154(b) by 262 days.

(21) Appl. No.: 10/292,414

(22) Filed: Nov. 11, 2002

(65) Prior Publication Data

US 2003/0105502 A1 Jun. 5, 2003

Related U.S. Application Data

(60) Provisional application No. 60/350,490, filed on Nov. 13, 2001.

(51) Int. Cl.[7] .................................................. A61N 1/18
(52) U.S. Cl. ..................................... 607/50; 607/117
(58) Field of Search ............................. 607/43, 48, 50, 607/117, 118

(56) References Cited

U.S. PATENT DOCUMENTS

| 4,919,140 A | 4/1990 | Borgens et al. |
| 5,417,719 A | 5/1995 | Hull et al. |

OTHER PUBLICATIONS

Notification of Transmittal of The International Search Report or the Declaration PCT/US02/36058.

Primary Examiner—Jeffrey R. Jastrzab
(74) Attorney, Agent, or Firm—Richard M. Lehrer; Mintz Levin Cohn Ferris Glovsky and Popeo PC

(57) ABSTRACT

An apparatus for stimulating regeneration and repair of damaged spinal nerves, comprising at least two electrodes placed intravertebrally near the site of spinal axon injury and delivering DC current thereto. A method for stimulating regeneration and repair of damaged spinal nervous tissue, comprising placing electrodes intravertebrally near the site of spinal cord injury and applying DC current at a level sufficient to induce regeneration and repair of damaged spinal axons but less than the current level at which tissue toxicity occurs.

6 Claims, 5 Drawing Sheets

Relative Distance Across
A Single Electrode Surface

APPARATUS AND METHOD FOR REPAIR OF SPINAL CORD INJURY

CROSS-REFERENCE TO RELATED PATENT APPLICATIONS

This application claims priority from Provisional Application Ser. No. 60/350,490, filed Nov. 13, 2001, now abandoned.

STATEMENT REGARDING FEDERALLY SPONSORED RESEARCH OR DEVELOPMENT

Not Applicable.

BACKGROUND OF THE INVENTION

1. Field of the Invention

The present invention relates to an apparatus and method for repairing spinal cord injury, and specifically an apparatus and method for stimulating regeneration and repair of damaged spinal nervous tissue.

2. Discussion of the Related Art

Spinal cord injury occurs when axons or nerve fibers of the spinal cord are interrupted, generally by mechanical forces. If the spinal cord is compressed, severed or contused, the axons may be physically or physiologically disintegrated, so that no conduction of neuroelectric impulses can occur along the affected axon's length. Eventually, large populations of axons, including their associated cell bodies, may die, causing massive loss in communication between the brain and the peripheral nerves, and resulting in varying degrees of paraplegia or quadriplegia.

Studies show that spinal cord injuries may be repaired if damaged spinal axons can be induced to regenerate. Such regeneration and repair can be induced by electric field stimulation, provided that the electric field is produced by direct current (DC). The DC field serves to promote a regenerative phenomenon that appears to be initiated by all axons, and also serves to guide axons toward the cathode of the electric field. As axons appear to respond to the field strength of exogenously applied fields, as opposed to the total current or voltage applied, axonal growth and directional guidance are the key effects of DC electric field application.

Axonal growth and directional guidance are not well understood. It is thought that there may be an optimum electric field strength for regeneration and repair, while directionality is a function of the flux density, electric gradient, and the orientation of the flux lines produced by the electric field. Unfortunately, the density at which unbalanced direct current can be applied to nervous tissue is finite, with the upper limit being the level of toxicity where significant cell damage occurs. The maximum safe current is approximately 75 $\mu$A at the electrode-tissue interface.

Existing electrode designs have attempted to minimize localized toxic effects of current application to the spinal cord by using extravertebral electrodes. However, extravertebral electrodes require significant amounts of power to produce meaningful field strengths within the damaged spinal cord. This is because extravertebral placement of the electrodes means that the anode and cathode are physically remote from the site of injury. As a result, more power is required to deliver the requisite current to the injury site, potentially resulting in toxic effects to surrounding tissues, such as muscle, nerves and blood vessels. It is understood that regeneration and repair of spinal axons is meaningless if the muscles to be controlled or their associated blood vessels and nerves are damaged as a result.

Further, extravertebral placement of electrodes necessitates situating the electrodes lateral to the site of the spinal cord injury, rather than in line therewith, resulting in less than optimal directional axonal guidance by the cathodal current. Still further, extravertebral placement of electrodes affects the extent to which the electrical flux lines generated by the electrodes deviate from the ideal, which itself is a major determinant in the quality of the electrical field established in the spinal cord. When electrodes are situated in extravertebral muscle, the flux lines within the spinal cord can be distorted from ideal by each intervening tissue that has a resistivity/conductivity differing from that of the muscle. The tissues that vary in these parameters and through which the current must pass, in the case of extravertebral placement of electrodes, include bone, ligaments, fat, cerebrospinal fluid, and vasculature. These structures may act as additional resistance or current shunts that can serve to deviate the resulting electric field within the spinal cord from a nominal field. Extravertebral field application is rendered significantly less reliable and thus less efficacious as the result of the difficulty in predicting the effects of the different resistivity/conductivity parameters of the intervening tissues.

What is needed is an apparatus and method for stimulating regeneration and repair of damaged spinal axons whereby control over the local electric field within the spinal cord is optimized, and toxicity to the central nervous system (CNS) and other tissues is minimized.

Accordingly, the present invention provides an apparatus suited to intravertebral implantation at the site of spinal cord injury, that allows DC stimulation of the injury site sufficient to induce regeneration and repair of damaged axons, but at a current below the non-toxic level of 75 $\mu$A/cm$^2$.

The present invention also provides a method for stimulating regeneration and repair of damaged spinal axons through intravertebral implantation of electrodes at the site of spinal cord injury, and subsequent DC stimulation at the injury site sufficient to induce regeneration and repair of the damaged axons, but at a current level below the level at which tissue toxicity occurs.

BRIEF SUMMARY OF THE INVENTION

An aspect of the present invention includes at least two electrodes configured to be placed intravertebrally proximal to the site of spinal axon injury and deliver DC current thereto. Each electrode includes an aggregate conductive electrode surface sufficiently large such that the current density from the electrode surface will induce axon regeneration and repair without damaging the surrounding tissue. In a preferred embodiment, the aggregate electrode surface includes multiple conductive sub-surfaces. The conductive sub-surfaces are separated from each other by non-conducting septa to minimize the production and dissipate any toxic product developed as the result of the delivery of electric current.

Another aspect of the present invention includes placing the electrodes of the present invention intravertebrally proximal the site of spinal cord injury and applying DC current at a level sufficient to induce regeneration and repair of damaged spinal axons but less than the current level at which tissue toxicity occurs. The current is applied for a duration sufficient to prevent significant die-back and thereby achieve net growth.

In a preferred embodiment, the electrodes are arrayed so as to encompass a cross-sectional area of the spinal cord, in the area of the spinal axon injury. In another preferred embodiment, the electrodes are arrayed in a three-dimensional geometry, such as a triangle, surrounding the site of spinal axon injury.

In one aspect of the present invention, the DC current is applied for sufficient duration to prevent significant dieback, ensuring that forward-direction axon regeneration and repair prevails over die-back.

DETAILED DESCRIPTION OF THE INVENTION

The apparatus for stimulating regeneration and repair of damaged spinal nerves of the present invention includes at least two electrodes that are configured to be placed intravertebrally proximal the site of spinal axon injury and deliver DC current thereto. The electrodes include an aggregate conductive electrode surface through which the DC current is delivered to the injury site. The aggregate conductive electrode surface is sufficiently large so that the density of the delivered DC current can induce axon regeneration and repair without generating a significant amount of toxic product in surrounding tissues.

Figure 1:
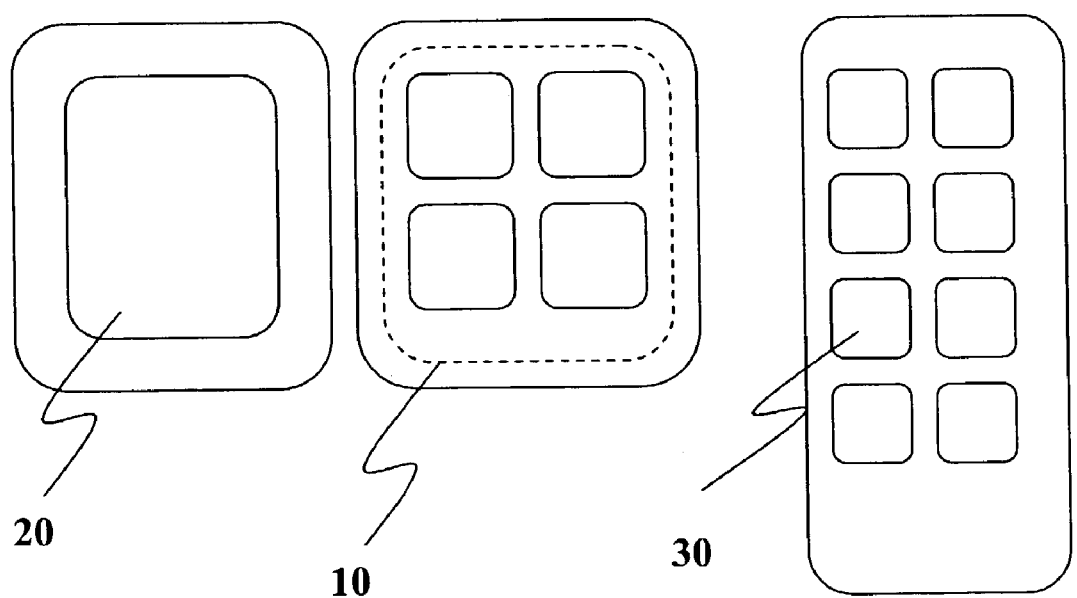
FIG. 1 depicts three preferred configurations for the aggregate conductive electrode surface of the apparatus of the present invention.
Figure 2:
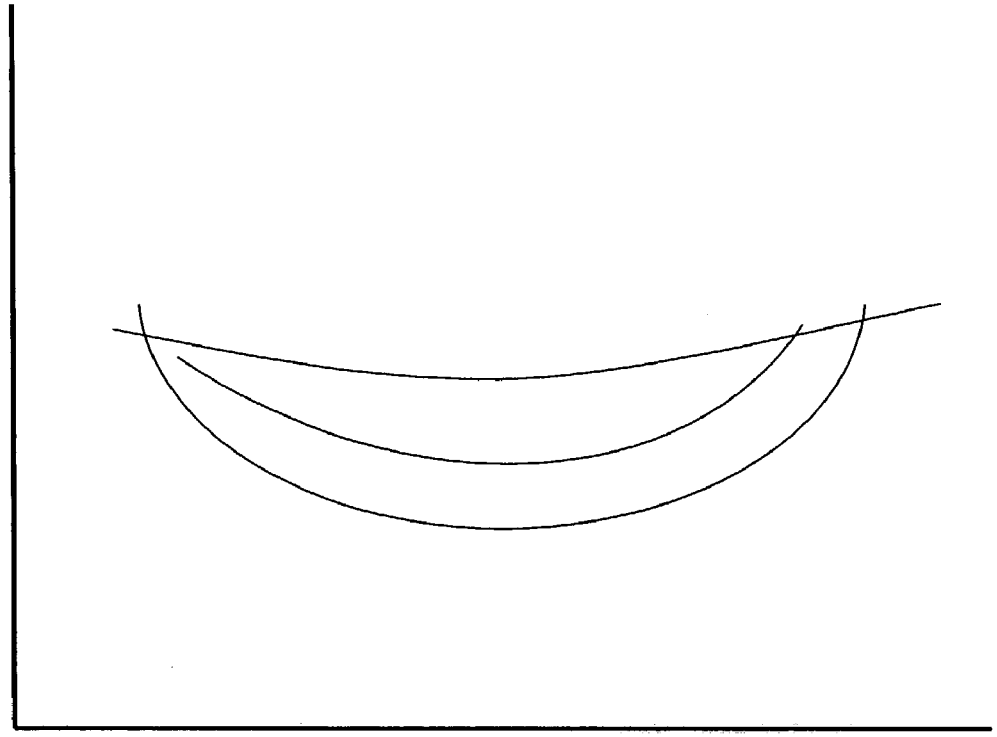
FIG. 2 is a graph of the electrode current profile across a single conductive electrode surface as a function of the relative distance across a single conductive electrode surface for each configuration depicted in FIG. 1.

As shown in FIG. 1, the aggregate conductive electrode surface 10 may include a single conductive surface 20 or multiple conductive sub-surfaces 30. Where multiple conductive sub-surfaces 30 are used, the result is a flattening of the trans-surface current gradient, or "skin effect," across each sub-surface. As shown in FIG. 2, the benefit is that regeneratively efficacious currents can be delivered to the injury site while minimizing the delivery of toxic peak currents. In FIG. 2, the uppermost curve shows the "skin effect" for multiple conductive sub-surfaces. The middle curve shows the "skin effect" for a small number of conductive sub-surfaces, and the lowermost curve shows the "skin effect" for a single conductive sub-surface.

Figure 3:
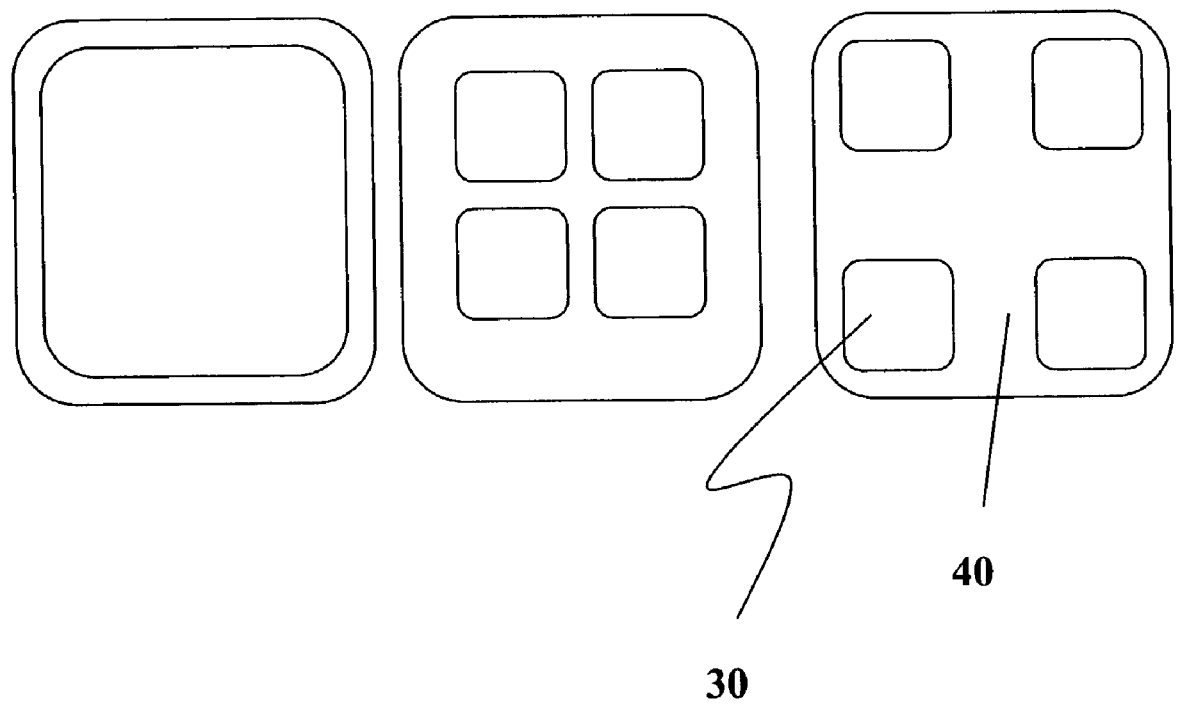
FIG. 3 depicts the electrode surface of the apparatus of the present invention, showing various patterns of separation between adjacent conductive sub-surfaces on the conductive electrode surface.
Figure 4:
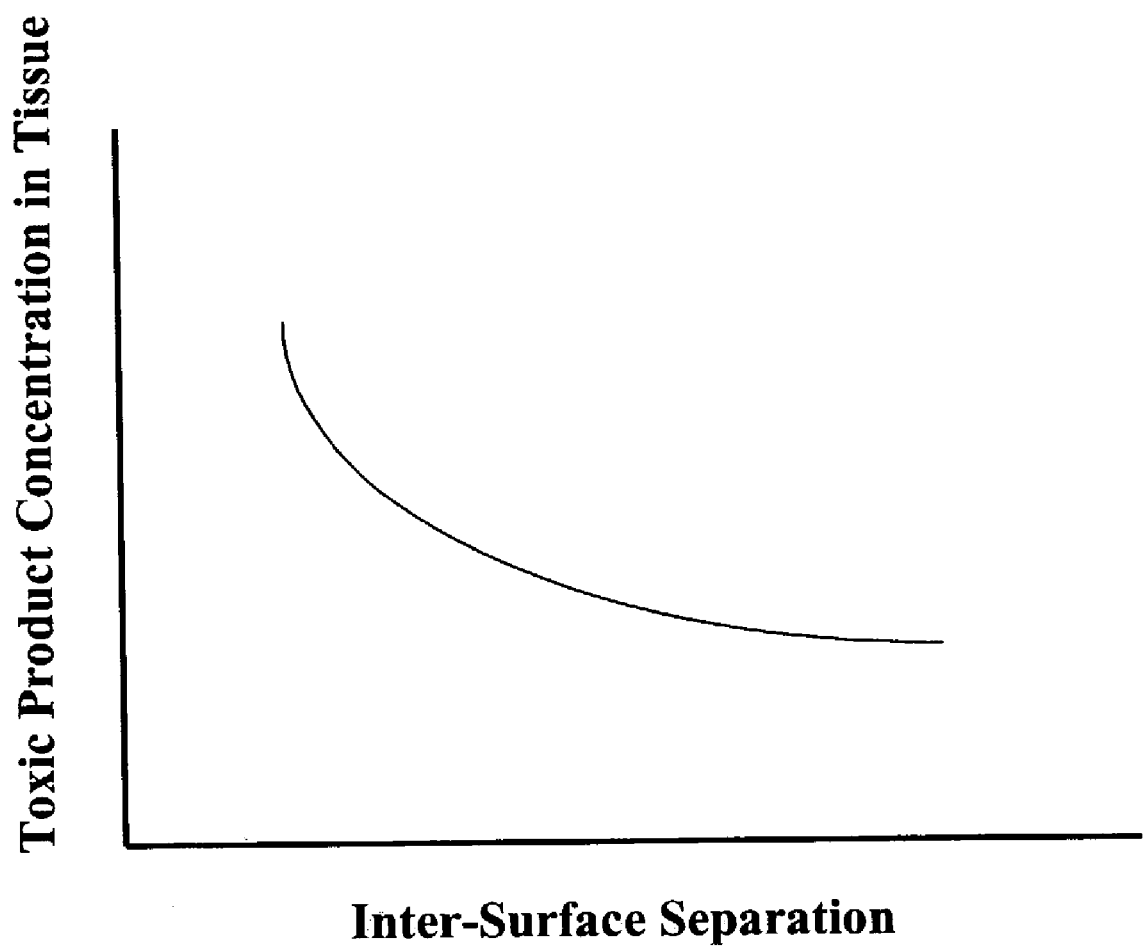
FIG. 4 is a graph of the relationship of toxic product concentration in the tissue as a function of the separation between adjacent conductive sub-surfaces on the conductive electrode surface.
Figure 5:
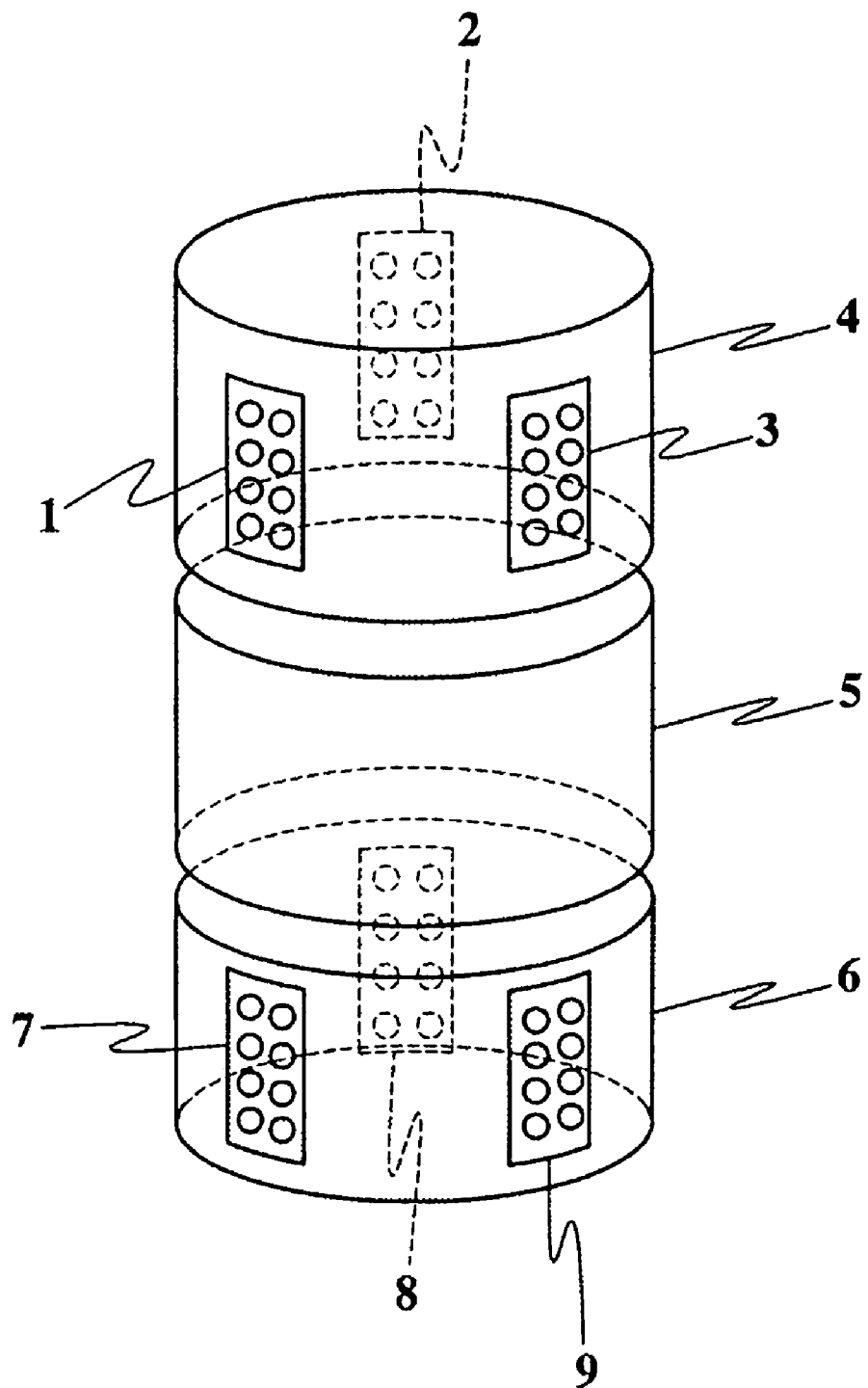
FIG. 5 is a schematic representation of one embodiment of the invention. 1, 2, 3, 7, 8 and 9 represents intravertebral electrodes intravertebrally implanted in a triangle arrangement. 4, 5 and 6 are three segments of the spinal cord where 5 is a segment comprising an injury. It is understood that the invention is not limited to FIG. 5, which is merely one embodiment of the invention. Many other embodiments are envisioned and described throughout this disclosure.

Further where the aggregate electrode surface includes multiple conductive sub-surfaces 30, adjacent sub-surfaces 30 are separated by non-conducting septa 40, as shown in FIG. 3. The left figure shows no septum between conductive surfaces. The center figure shows a small septum between the adjacent conductive surfaces. The right figure shows a large nonconductive septum between adjacent conductive subsurfaces. The specific geometry of the non-conducting septa 40 relative to the conductive sub-surfaces 30 may vary as required to optimize the contribution of the septal effect. Specifically, interposing non-conducting septa 40 between adjacent sub-surfaces 30 reduces the concentration, in surrounding tissues, of any toxic product developing as a result of the delivery of electric current through the electrode, by virtue of the dissipation of the toxic product across the total area of the entire aggregate conductive electrode surface 10. The aggregate electrode surface includes conductive surfaces, either a single conductive surface 20 or multiple conductive sub-surfaces 30, and non-conductive septa 40. FIG. 4 shows the relationship between the dilution of toxic product and the size of the non-conductive septa. The non-conducting septa 40 may constitute empty space between adjacent conductive sub-surfaces 30.

The apparatus of the present invention may also be arrayed for use in neural systems having multi-directional axonal elements. In such systems, the electrical field may be applied sequentially along the direction of each damaged axon population. Accordingly, the location of stimulating electrodes can vary depending on the direction along which regeneration and repair is sought, so that discrete epidural multi-electrode surfaces can be used to stimulate axonal growth in a selective fashion. For example, it is known that dorsally-situated axons will regenerate rostrally, while corticospinal axons, situated laterally, will regenerate caudally. Thus, an intravertebral panel comprising a plurality of electrodes encompassing the cross-sectional area of the spinal cord can selectively produce cathodally-directed current for longer periods of time over the axon tracts of interest.

Alternatively, electrodes may be configured in a three-dimensional geometry, such that the aggregate electrode stimulation through multiple electrodes can generate an effective electrical field along any desired vector.

The number of electrodes in a given paradigm, the specific geometric placement of the electrodes, and the aggregate use of a plurality of electrodes may vary according to the demands of the therapeutic challenge for which DC stimulation is being applied.

According to the method of the present invention, the electrodes as described are placed intravertebrally proximal to the site of spinal axon injury. Once the electrodes are so placed and properly arrayed, a DC current is delivered through the electrodes to the injury site, inducing regeneration and repair of spinal axons. The current density of the delivered DC current is sufficient to induce axon regeneration and repair while avoiding tissue toxicity. Preferably, the current density at the electrode-tissue interface is less than 75 $\mu$A/cm$^2$. As relatively high resistivity tissues such as bone and fat are located distal to the desired locus of electrical field regeneration and repair, in intravertebral stimulation the bone, fat and meninges serve as a natural physical guidance means to provide a directional path for axonal regeneration and repair. In this way, intravertebral regeneration and repair may represent an improvement over nerve regeneration and repair systems in which a physical guidance system is actively employed. At the same time, intravertebral electrode placement allows the safe delivery of higher currents to the injury site, so that higher field strengths can be injected thereto. Since the electrodes are applied locally, the relative amount of current delivered can be low, relative to extravertebral electrodes, and yet may achieve field strengths higher than extravertebral electrodes can achieve.

The duration of electrical stimulation is sufficient to prevent significant "die-back" phenomenon, as explained by McCaig, in "Spinal Neurite Reabsorption and Regrowth in vitro Depend on the Polarity of an Applied Electric Field," *Development* 100, 31–41 (1987), and which is incorporated herein by reference. The optimal stimulation duration will depend upon the specific therapeutic application. The duration will be sufficient to ensure that the forward-direction regenerative axon growth prevails over the "die-back" effect.

DC stimulation of damaged spinal axons may be used as a stand-alone regenerative and repair therapy, or may be used as an adjunct to other therapies, whether presently available or to become available in the future. Such therapies include, but are not limited to, pharmaceutical, genetically-engineered, biological, surgical, psycho- and physical therapies.

The electrode, including the electrode surface, may be made from conventional materials. The DC current may be generated from any conventional DC generator used in biotherapeutic applications.

While the invention has been described with respect to certain specific embodiments, it will be appreciated that many modifications and changes may be made by those skilled in the art without departing from the invention. It is intended, therefore, by the appended claims to cover all such modifications and changes as may fall within the true spirit and scope of the invention.

What is claimed is:

1. A method for stimulating regeneration and repair of damaged spinal nervous tissue, comprising the steps of:
   a. arraying electrodes intravertebrally, proximal to a site of spinal cord injury;
   b. applying a direct current ("DC") from a DC source through said electrodes to said site of spinal cord injury, where a current density level of the DC current is sufficient to induce regeneration and repair of damaged spinal nervous tissue but less than the current density level at which tissue toxicity occurs; and
   c. applying direct current from a DC source for a duration sufficient to induce forward-direction regeneration and repair of said damaged spinal nervous tissue and prevent significant die-back.

2. The method of claim 1, wherein the electrodes are arrayed so as to encompass a cross-sectional area of the spinal cord, proximal to the site of spinal cord injury.

3. The method of claim 1, wherein the electrodes are arrayed in a three-dimensional geometry configured and arranged to surround the site of spinal cord injury.

4. The method of claim 3 wherein the electrodes are arranged to encompass a cross sectional area of the spinal cord.

5. The method of claim 3 wherein the electrodes are arranged in a triangle.

6. The method of claim 1, wherein the current density is less than 75 $\mu A/cm^2$ at an electrode-tissue interface.

* * * * *